(12) United States Patent
Jirtle et al.

(10) Patent No.: US 6,218,127 B1
(45) Date of Patent: Apr. 17, 2001

(54) CANCER PROGNOSIS WITH THE M6P/IGF-II RECEPTOR

(75) Inventors: Randy L. Jirtle; Timothy A. Jamieson; J. Keith Killian, all of Durham, NC (US)

(73) Assignee: Duke University, Durham, NC (US)

(*) Notice: Subject to any disclaimer, the term of this patent is extended or adjusted under 35 U.S.C. 154(b) by 0 days.

(21) Appl. No.: 09/527,443

(22) Filed: Mar. 17, 2000

Related U.S. Application Data

(60) Provisional application No. 60/124,892, filed on Mar. 18, 1999.

(51) Int. Cl.[7] .............................. C12Q 1/68; C12P 19/34; C07H 21/04
(52) U.S. Cl. ........................ 435/6; 435/91.2; 536/23.1; 536/23.5
(58) Field of Search ................... 435/6, 91.2; 536/23.1, 536/23.5

(56) References Cited

PUBLICATIONS

De Souza et. al., "M6P/IGF2R gene is mutated in human hepatocellular carcinomas with loss of heterozygosity". Nature Genetics (1995) 11: 447–449.*

Lewin et. al., "Neoajuvant chemotherapy with cisplatin and 5–fluorouracil in advanced squamous cell carcinoma of the head and neck". Radiotherapy and Oncology (1997) 43: 23–28.*

Brizel et. al., "Hyperfractionated irradiation with or without concurrent chemotherapy for locally advanced head and neck cancer". New England Journal of Medicine (1998) 338: 1798–1804.*

* cited by examiner

Primary Examiner—Carla J. Myers
Assistant Examiner—Alexander H. Spiegler
(74) Attorney, Agent, or Firm—Nixon & Vanderhye P.C.

(57) ABSTRACT

The present invention relates, in general, to cancer prognosis and, in particular, to a method of assessing the prognosis of a patent using the M6P/IGF-II receptor.

3 Claims, 4 Drawing Sheets

CANCER PROGNOSIS WITH THE M6P/IGF-II RECEPTOR

This application claims the benefit of U.S. Provisional Application No. 60/124,892, filed Mar. 18, 1999, the entire content of which is hereby incorporated by reference in this application.

This invention was made with Government support under Grants CA25951 and ES08823 awarded by the National Institutes of Health, and under Grant DAMD17-98-1-8305 awarded by the Department of Defense. The Government may have certain rights in the invention.

TECHNICAL FIELD

The present invention relates, in general, to cancer prognosis and, in particular, to a method of assessing the prognosis of a patent using the M6P/IGF-II receptor.

BACKGROUND

Squamous cell carcinoma of the head and neck is diagnosed in over 40,000 Americans each year, resulting in over 12,000 annual deaths (Parker et al, CA Cancer J. Clin. 46: 5–27 (1996)). Carcinomas of the head and neck are often associated with multiple areas of dysplasia or carcinoma in situ (CIS) in noncontiguous mucosa, as well as with the development of second primary cancers of the aerodigestive tract. This concept of "field cancerization" was introduced by Slaughter in 1953, hypothesizing that the epithelium becomes "preconditioned" from exposure to carcinogenic agents, thus priming it for subsequent development of invasive lesions after additional genetic hits occur (Slaughter et al, Cancer. 6: 963–968 (1953)).

Modern molecular biological techniques have supported and greatly expanded the knowledge of the "cancer field effect". Specifically, it has been demonstrated by analysis of X-chromosome inactivation in female patients with multiple head and neck cancers that distinct tumors may arise from the regional clonal growth of phenotypically normal, mutated preneoplastic cells (Bedi et al, Cancer Res. 56: 2484–2487(1996)). Chromosomal studies evaluating for loss of heterozygosity (LOH) in hyperplastic, dysplastic, CIS, and invasive lesions have identified that LOH at loci on 9p21-22 (corresponding to the cyclin-dependent kinase inhibitor, p16, as well as other possible tumor suppressor genes) and 3p (with three possible tumor suppressor genes) occurs early in tumor promotion (Waber et al, Oncogene. 15: 1699–704 (1997), Califano et al, Cancer Res. 56: 2488–2492 (1996)). Inactivation of p53 through LOH and subsequent mutation of the remaining allele has also been shown to occur in the progression from preinvasive to invasive carcinoma (Califano et al, Cancer Res. 56: 2488–2492 (1996)). Allelic loss at 4q26-28, 6p, 8p, 8q, 11q13, 13q, 14q31-32.1 and more recently 2q has also been observed in head and neck cancer (Bedi et al, Cancer Res. 56: 2484–2487(1996), Waber et al, Oncogene. 15: 1699–704 (1997), Califano et al, Cancer Res. 56: 2488–2492 (1996), Nawroz et al, Cancer Res. 54: 1152–5 (1994), Yoo et al, Cancer Res. 54: 4603–6 (1994), Ransom et al, Head Neck. 20: 404–10 (1998), Lydiatt et al, Head Neck. 20: 113–8 (1998), Callender et al, Cancer. 74: 152–8 (1994)).

The mannose-6-phosphate/insulin-like growth factor 2 receptor (M6P/IGF-II receptor) is a tumor suppressor located on 6q26 that has been shown to be inactivated in breast, liver and lung cancer (De Souza et al, Oncogene. 10: 1725–9 (1995), De Souza et al, Nat. Genet. 11: 447–9 (1995), Yamada et al, Proc. Natl. Acad. Sci. USA. 94: 10351–5 (1997), Hankins et al, Oncogene. 12: 2003–9 (1996)). This receptor regulates cell growth by binding and inactivating the mitogen, IGF2, and activating the growth inhibitor, transforming growth factor beta (TGFβ) (De Bleser et al, Hepatology. 21: 1429–37 (1995), Dennis et al, Proc. Natl. Acad. Sci. USA. 88: 580–4 (1991), Kornfeld et al, Annu. Rev. Biochem. 61: 307–330 (1992)). The M6P/IGF-II receptor has also been shown to be mutated in gastrointestinal and endometrial malignancies with mismatch repair enzyme deficiencies and microsatellite instability (Souza et al, Nat. Genet. 14: 255–257 (1996), Ouyang et al, Cancer Res. 57: 1851–1854 (1997)). Furthermore, chronic hepatitis virus infection of the liver results in the inactivation of a single allele of the M6P/IGF-II receptor, and the clonal expansion of normal appearing, M6P/IGF-II receptor-mutated preneoplastic hepatocytes from which the majority of HCCs ultimately develop (Yamada et al, Proc. Natl. Acad. Sci. USA. 94: 10351–5 (1997)). Thus, M6P/IGF-II receptor inactivation occurs frequently and early in liver carcinogenesis.

The present invention results from the demonstration that LOH occurs at the M6P/IGF-II receptor locus in over 50% of head and neck cancers and that this LOH is predictive of a poor therapeutic outcome.

SUMMARY OF THE INVENTION

The present invention relates to a method of assessing the prognosis of a patient using the M6P/IGF-II receptor. The method makes possible the prospective determination of patients likely to benefit from adjuvant therapy.

Objects and advantages of the present invention will be clear from the description that follows.

DETAILED DESCRIPTION OF THE INVENTION

Figure 1:
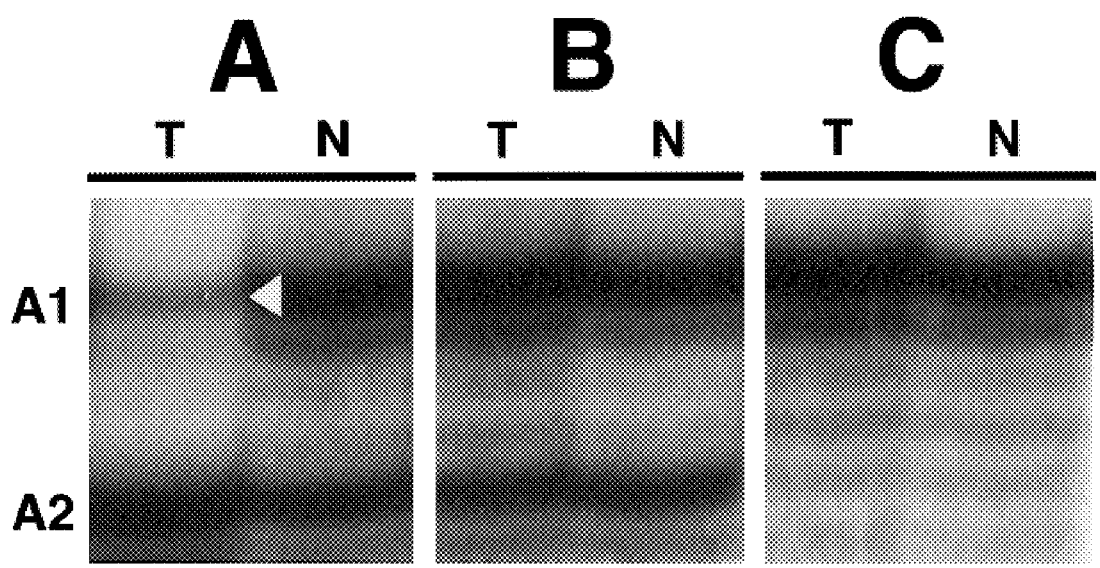
FIG. 1: LOH at the M6P/IGF-II receptor locus in human squamous cell carcinomas of the head and neck. A) An informative patient at the tetranucleotide (ACAA) insertion/deletion polymorphism in the 3'-UTR of the M6P/IGF-II receptor gene (Hol et al, Hum. Mol. Genet. 1:347 (1992)) with LOH in the tumor. The white arrow head marks the lost allele; the faint band is due to contaminating normal stromal tissue. B) An informative patient without LOH in the tumor. C) A non-informative patient. The 2 alleles are defined as A1 and A2 for the informative patients. N, normal stromal tissue; T, tumor.

The M6P/IGF-II receptor functions in the intracellular trafficking of lysosomal enzymes, the activation of the growth inhibitor, TGFβ, and the degradation of IGF2, but it is not directly involved in cell signaling (Kornfeld et al, Annu. Rev. Biochem. 61: 30–330 (1992), Körner et al, J. Biol. Chem. 270: 287–95 (1995)). Thus, the M6P/IGF-II receptor functions as a "guardian of the cell" by controlling the extracellular levels of potent growth factors and proteolytic enzymes that govern cell death, proliferation and invasion suggesting the M6P/IGF-II receptor is a tumor suppressor. This postulate is supported by the finding that inactivation of the M6P/IGF-II receptor gene is a frequent early event in both liver and breast carcinogenesis (De Souza et al, Oncogene. 10: 1725–9 (1995), De Souza et al, Nat. Genet. 11: 447–9 (1995), Yamada et al, Proc. Natl. Acad. Sci. USA. 94: 10351–5 (1997), Hankins et al, Oncogene. 12: 2003–9 (1996)).

In the study that resulted in the present invention, the importance of the M6P/IGF-II receptor in head and neck cancer was investigated by determining the frequency of LOH at this locus, and correlating gene loss with patient survival following radiation therapy alone or in combination with chemotherapy. As will be clear from the Example that follows, LOH at the M6P/IGF-II receptor locus occurred in 54% of patients with squamous cell carcinoma of the head and neck adding 6q to the list of chromosomal regions harboring one or more tumor suppressors for head and neck cancer. Following radiotherapy alone, 5 year cause specific survival, failure free survival and locoregional control were significantly reduced in patients in whose head and neck cancers the M6P/IGF-II receptor gene was mutated.

The Duke University Medical Center's randomized prospective trial of twice daily radiation therapy with or without concurrent fluorouracil and cisplatin demonstrated the superiority of concurrent chemotherapy in overall survival, failure free survival, and locoregional control in the 116 patients studied (Brizel et al, N. Engl. J. Med. 338: 1798–804 (1998)). In the subgroup of these patients studied retrospectively, the patients with tumors containing an unmutated M6P/IGF-II receptor gene did well regardless if chemotherapy was administered in addition to radiotherapy. In contrast, those patients who had a tumor with a mutated M6P/IGF-II receptor gene benefited markedly from the addition of concurrent chemotherapy with radiotherapy. These data indicate that M6P/IGF-II receptor gene mutation confers a decreased sensitivity to radiation that can be circumvented in part with the addition of chemotherapy. Although concurrent chemotherapy has become increasingly considered as standard care in the treatment of locally advanced disease, the present data indicate that it benefits only those patients with tumors that have a mutated M6P/IGF-II receptor gene.

Other chromosomal loci have been examined for LOH in head and neck cancers (Field, Anticancer Res. 16: 2421–31 (1996)). Patients with stage I or II head and neck cancer that ultimately failed therapy had a LOH frequency of 75% at chromosome 2q31-32 compared with a 20% frequency (p=0.03) in patients that did not fail therapy (Ransom et al, Head Neck. 20: 404–10 (1998)). A DNA mismatch repair gene, hPMS1, and/or a tumor suppressor gene at this chromosomal location may be mechanistically involved in head and neck cancer (Ransom et al, Head Neck. 20: 404–10 (1998)). Chromosome 3p contains at least three loci that may be involved in head and neck tumor formation (Maestro et al, Cancer Res. 53: 5775–9 (1993)). LOH at 3p has been found in over 50% of head and neck cancers, and has been shown to correlate with an increased incidence of nodal and distant metastases, as well as decreased survival in early stage disease (Maestro et al, Cancer Res. 53: 5775–9 (1993), Field et al, Br. J. Cancer. 72: 1180–8 (1995), Partridge et al, Br. J. Cancer. 73: 366–71 (1996)).

LOH at 9p21-22 occurs in over 70% of head and neck cancers and contains the genes encoding the cyclin-dependent kinase inhibitors, p15 and p16 (Bedi et al, Cancer Res. 56: 2484–2487(1996), Field et al, Br. J. Cancer. 72: 1180–8 (1995), van der Riet et al, Cancer Res. 54: 1156–8 (1994)). These proteins induce a block at the G1/S checkpoint. Thus, loss of these genes would allow continuation through the cell cycle of genetically damaged cells that otherwise would undergo repair or apoptosis. LOH at 9p21 also correlates with increased tumor recurrence (80% vs. 24%) in the 32 surgically treated patients studied (Lydiatt et al, Head Neck. 20: 113–8 (1998)).

LOH in the region of the p53 locus at 17p13 occurs early in dysplastic lesions (Califano et al, Cancer Res. 56: 2488–2492 (1996)). Subsequent mutation of the remaining allele appears to be a later event, often occurring at the time of progression to invasive cancer. The p53 gene is mutated in over 40% of head and neck cancers and correlates with a history of heavy smoking (Field et al, Br. J. Cancer. 64: 573–7 (1991)) A recent report demonstrates both a 47% frequency of LOH of p53 and a 34% rate of amplification of the cyclin D1 gene (Nogueira et al, Laryngoscope. 108: 345–50 (1998)). These two events are additive in their association with increased recurrences and metachronous primary tumors in head and neck cancer.

The results of the studies described in the Example that follows are consistent with the M6P/IGF-II receptor gene also being mechanistically involved in the genesis of head and neck cancer. While LOH at the M6P/IGF-II receptor gene locus indicates that this gene is functioning as a tumor suppressor in head and neck cancer, other putative tumor suppressor genes that reside on 6q may also be the relevant targets of inactivation since LOH often results from a large chromosomal deletion that encompasses a number of genes. Frequent LOH at 6q23-27 has been demonstrated in a variety of tumors including those that develop in the breast, kidney, liver, lymph node, ovary and salivary gland (De Souza et al, Oncogene 10:1725–1729 (1995), Queimado et al, Oncogene 16:83–88 (1998)). Candidate tumor suppressor genes within 6q, in addition to the M6P/IGF-II receptor gene, include the manganese superoxide dismutase gene at 6q25.2 (Church et al, Proc. Natl. Acad. Sci. USA 90:3113–3117 (1993)), the zinc finger transcription factor, Lot1 (hZAC), located at 6q24-q25 that induces $G_1$ arrest and apoptosis (Varrault et al, Proc. Natl. Acad. Sci. USA 95:8835–8840 (1998), Abdollahi et al, Oncogene 14:1973–1979 (1997)), SEN6 that is involved in the immortalization of cells after infection with the virus SV40 (Banga et al, Oncogene 14:313–321 (1997)), and a novel extracellular ribonuclease at 6q27 that is highly conserved from plants to humans and may play a critical role in growth regulation (Trubia et al, Genomics 42:342–344 (1997)).

Summarizing, LOH at the M6P/IGF-II receptor locus occurred in over half of the squamous cell carcinomas of the head and neck studied indicating that it functions as a tumor suppressor in head and neck cancer. Furthermore, mutation of the M6P/IGF-II receptor gene is correlated with poor locoregional control and patient survival following treatment of locally advanced tumors with radiation therapy. These findings provide basis for a method of assessing the prognosis of a patient bearing a squamous cell carcinoma of the head or neck, that method comprising screening for mutations (e.g., LOH) at the M6P/IGF-II receptor locus.

Certain aspects of the present invention are described in greater detail in the non-limiting Example that follows.

EXAMPLE
EXPERIMENTAL DETAILS

Patients. One hundred and sixteen patients with locally advanced head and neck squamous cell carcinoma who were enrolled in a Duke University Medical Center protocol of definitive twice daily radiotherapy with or without concurrent chemotherapy were analyzed in this study. DNA could not be PCR amplified from 11 of the tumors, and these patients were therefore excluded from further analysis. Tumors were histologically confirmed.

Tissue Microdissection and LOH Analysis. Microdissection of malignant and surrounding normal non-mucosal tissue was performed as previously described (De Souza et al, Oncogene 10:1725–1729 (1995), De Souza et al, Nat. Genet. 11:447–449 (1995), Yamada et al, Proc. Natl. Acad. Sci. USA 94:10351–10355 (1997), Hankins et al, Oncogene 12:2003–2009 (1996)). Briefly, 10 μm paraffin sections were microdissected and the tissue digested by proteinase K in Tris-EDTA buffer at 55° C. for 4 hr. A tetranucleotide (ACAA) insertion/deletion polymorphism in the 3'-UTR of the M6P/IGF-II receptor gene (Hol et al, Hum. Mol. Genet. 1:347 (1992)), and 5 identified single nucleotide polymorphisms at locations 901 (C/G), 1197 (A/G), 1737 (G/A), 2286 (A/G) and 5002 (G/A) were used to determine LOH at this locus. The DNA regions containing these polymorphisms were amplified by 2 rounds of nested PCR performed with Platinum® Taq DNA polymerase (GibcoBRL, Baltimore, Md.) using primer pairs described previously (Hol et al, Hum. Mol. Genet. 1:347 (1992), Killian et al, Mamm. Genome 10:74–77 (1999)). Each round of PCR consisted of 31 cycles of 94° C. for 20 seconds, 55° C. for 40 seconds, and 72° C. for 45 seconds. The PCR product containing the 3'-UTR insertion/deletion polymorphism was electrophoresed on a 6% acrylamide gel and exposed to film (FIG. 1). The single nucleotide polymorphisms were used to assess for tumor LOH following direct sequencing of PCR products according to the manufacturer's protocol (Thermo Sequenase, USB Corporation, Cleveland Ohio).

Treatment Protocol. Patients were treated as previously described (Brizel et al, N. Engl. J. Med. 338:1798–1804 (1998)). Briefly, patients with locally advanced head and neck cancer were randomized to radiotherapy alone or combined modality. Radiotherapy alone consisted of a 75 Gy primary tumor dose using 125 cGy b.i.d. fractionation, and 40 Gy to the uninvolved nodal areas. Combined modality therapy consisted of 70 Gy primary tumor dose using 125 cGy b.i.d. with concurrent chemotherapy during weeks 1 and 6 of radiotherapy. The chemotherapy consisted of continuous fluorouracil infusion at 600 mg/m$^2$ surface for 5 days and 60 mg/m$^2$ cisplatin given in a 12 mg/m$^2$ daily bolus for 5 consecutive days.

Statistical Analysis. Survival curves were constructed using the Kaplan-Meier method. Survival curves begin at the time of entry into the study. The survival of pairs of subgroups were tested for differences by the Cox-Mantel test; cause specific survival (CSS), failure free survival (FFS), and locoregional control (LRC) were analyzed.

RESULTS

M6P/IGF-II receptor LOH Analysis. One hundred and five patients with squamous cell carcinoma of the head and neck who were enrolled on the b.i.d. radiotherapy protocol (Brizel et al, N. Engl. J. Med. 338:1798–1804 (1998)) were screened for LOH at the M6P/IGF-II receptor gene locus. Forty-eight (46%) patients were informative, and LOH at the M6P/IGF-II receptor gene locus (FIG. 1) was found in 54% (26/48) of the tumors. The patient characteristics of the 26 LOH and 22 non-LOH patients were similar in tumor stage, treatment received and age (Table 1).

Figure 2:
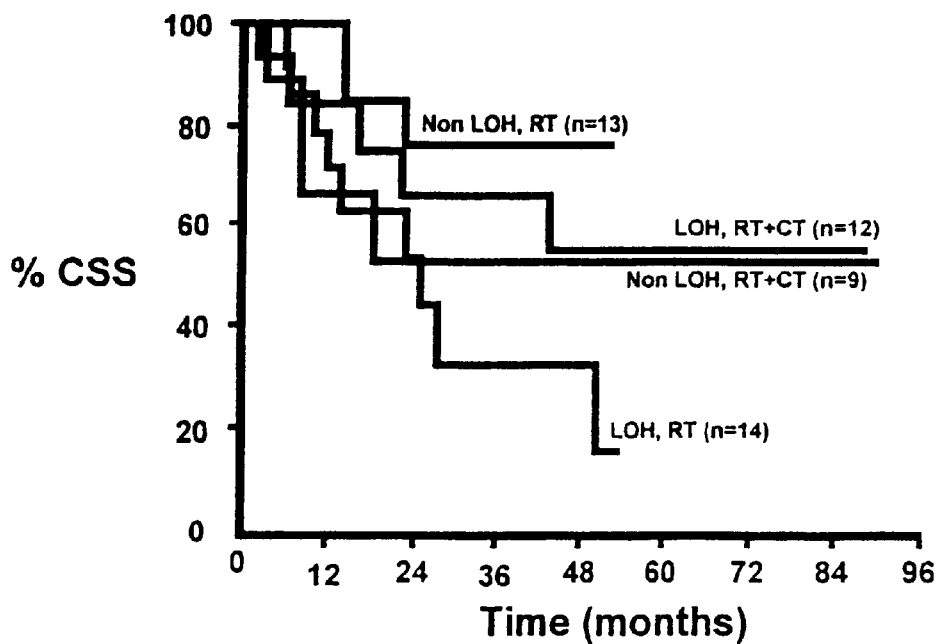
FIG. 2: Kaplan-Meier estimate of cause specific survival (CSS) in patients with the M6P/IGF-II receptor gene mutated in head and neck cancers treated with RT alone (LOH, RT) or combined modality (LOH, RT+CT), and in those patients without M6P/IGF-II receptor gene mutation receiving RT alone (non LOH, RT) or combined modality (non LOH, RT+CT). LOH, loss of heterozygosity; RT, radiotherapy; and CT, chemotherapy.
Figure 3:
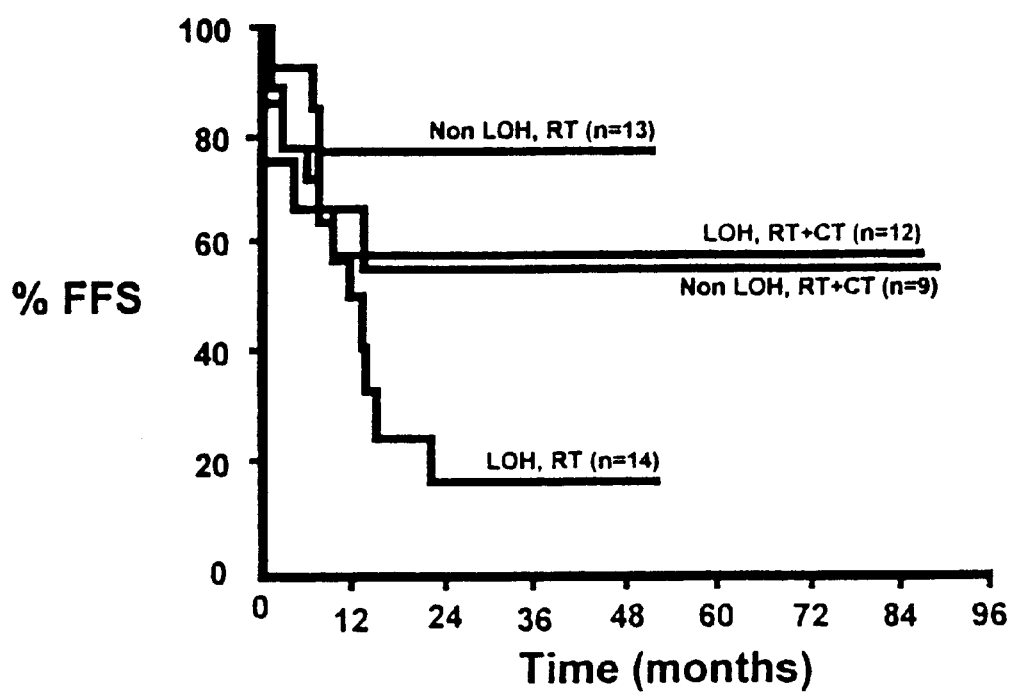
FIG. 3: Kaplan-Meier estimate of failure free survival (FFS) in patients with the M6P/IGF-II receptor gene mutated in head and neck cancers treated with RT alone (LOH, RT) or combined modality (LOH, RT+CT), and in those patients without M6P/IGF-II receptor gene mutation receiving RT alone (non LOH, RT) or combined modality (non LOH, RT+CT). LOH, loss of heterozygosity; RT, radiotherapy; and CT, chemotherapy.
Figure 4:
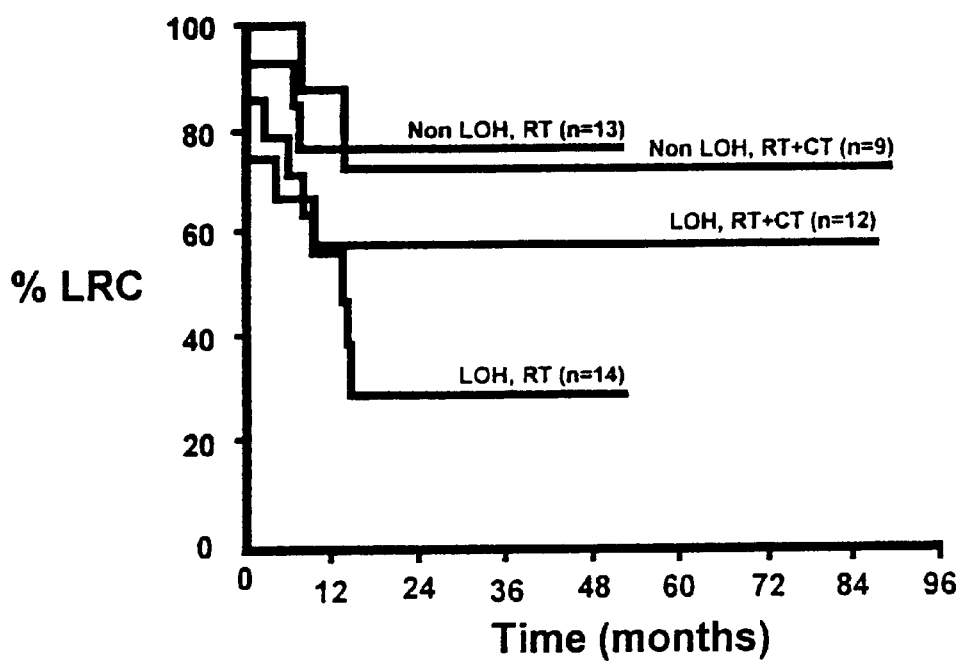
FIG. 4: Kaplan-Meier estimate of locoregional control (LRC) in patients with the M6P/IGF-II receptor gene mutated in head and neck cancers treated with RT alone (LOH, RT) or combined modality (LOH, RT+CT), and in those patients without M6P/IGF-II receptor gene mutation receiving RT alone (non LOH, RT) or combined modality (non LOH, RT+CT). LOH, loss of heterozygosity; RT, radiotherapy; and CT, chemotherapy.

Survival and Locoregional Control Analysis. The 48 informative patients were analyzed for CSS, FFS and LRC. Those with LOH at the M6P/IGF-II receptor gene locus demonstrated decreased actuarial 5 yr CSS (38% vs. 67%, p=n.s.), 5 yr FFS (38% vs. 68%, p=0.057) and 5 yr LRC (45% vs. 76%, p=0.034). The addition of concurrent chemotherapy has been shown to significantly improve these parameters (Brizel et al, N. Engl. J. Med. 338:1798–1804 (1998)). Therefore, the CSS, FFS and LRC were also determined in the LOH and non-LOH patients treated with or without chemotherapy (FIGS. 2–4). The LOH patients receiving RT alone had significantly lower CSS (18% vs. 76%, p=0.040), FFS (17% vs. 77%, p=0.007) and LRC (29% vs. 77%, p=0.036) than the non-LOH patients receiving RT alone. The LOH patients receiving RT alone also had considerably lower CSS (18% vs. 55%), FFS (17% vs. 58%) and LRC (29% vs. 58%) than the LOH patients treated with combined modality, although the differences were not statistically significant in these small subgroups. LOH patients receiving combined modality therapy had CSS, FFS, and LRC that were statistically (p>0.2) indistinguishable from the non-LOH patients. Finally, chemotherapy did not provide a significant benefit (p>0.2) to radiation in patients without LOH.

Second Primary Analysis. No significant difference was seen in the development of second primaries in the LOH and non-LOH groups. Two of the 26 LOH patients and 2 of the 22 non-LOH patients developed second primaries. Among the LOH patients, one had a synchronous squamous cell carcinoma of the esophagus and another developed a poorly differentiated non small cell lung cancer 32 months after diagnosis of the initial squamous cell carcinoma of the tonsil. Second primaries were detected in both of the non-LOH patients 15 months after diagnosis of the initial head and neck cancer.

All documents cited above are hereby incorporated in their entirety by reference.

One skilled in the art will appreciate from a reading of this disclosure that various changes in form and detail can be made without departing from the true scope of the invention.

TABLE 1

Characteristics of the patients with and without LOH at the M6P/IGF2R locus.

| CHARACTERISTIC | LOH Group (n = 26) | Non-LOH Group (n = 22) |
|---|---|---|
| Median Follow-up (months) | 30 | 23 |
| Age (yr) | 60 ± 9* | 64 ± 10* |
| Tumor Stage (no.) | | |
| T2 | 1 | 6 |
| T3 | 13 | 10 |
| T4 | 12 | 6 |

TABLE 1-continued

Characteristics of the patients with and without LOH at the M6P/IGF2R locus.

| CHARACTERISTIC | LOH Group (n = 26) | Non-LOH Group (n = 22) |
|---|---|---|
| Nodal Stage (no.) | | |
| N0 | 9 | 8 |
| N1 | 5 | 3 |
| N2 | 10 | 10 |
| N3 | 2 | 1 |
| Treatment (no.) | | |
| RT alone | 14 | 13 |
| RT + chemotherapy | 12 | 9 |
| Site of Primary Tumor (no.) | | |
| Base of tongue | 6 | 7 |
| Tonsil | 6 | 4 |
| Larynx | 8 | 3 |
| Hypopharynx | 2 | 5 |
| Paranasal sinuses | 0 | 2 |
| Oral cavity | 3 | 1 |
| Soft palate | 1 | 0 |

*Standard Deviation

What is claimed is:

1. A method of identifying a patient bearing a head or neck squamous cell carcinoma who would benefit from a therapeutic regimen comprising radiation therapy and chemotherapy comprising:

i) isolating a sample of said carcinoma, ii) analyzing DNA in said sample for loss of heterozygosity (LOH) at the M6P/IGF-II receptor gene locus, wherein said LOH indicates that said patient would benefit from said therapeutic regimen.

2. The method according to claim 1 wherein said chemotherapy comprises administering fluorouracil and cisplatin.

3. The method according to claim 1 wherein said analysis of step (ii) is effected by screening for a tetranucleotide insertion/deletion polymorphism in the 3'-UTR of the M6P/IGF-II receptor gene and single nucleotide polymorphisms at locations 901, 1197, 1737, 2286 and 5002 of the M6P/IGF-II receptor gene.

* * * * *